United States Patent
Karpol et al.

(12) 
(10) Patent No.: US 6,267,477 B1
(45) Date of Patent: Jul. 31, 2001

(54) THREE DIMENSIONAL IMAGING APPARATUS AND A METHOD FOR USE THEREOF

(75) Inventors: Avner Karpol, Nes Ziona (IL); Ran Zeimer, Baltimore, MD (US)

(73) Assignee: Talia Technology Ltd., Mevasseret Zion (IL)

( * ) Notice: Subject to any disclaimer, the term of this patent is extended or adjusted under 35 U.S.C. 154(b) by 0 days.

(21) Appl. No.: 09/125,585
(22) PCT Filed: Feb. 20, 1997
(86) PCT No.: PCT/IL97/00065
§ 371 Date: Aug. 21, 1998
§ 102(e) Date: Aug. 21, 1998
(87) PCT Pub. No.: WO97/30627
PCT Pub. Date: Aug. 28, 1997

(30) Foreign Application Priority Data

Feb. 23, 1996 (IL) .......................................... 117241

(51) Int. Cl.[7] ....................................................... A61B 3/10
(52) U.S. Cl. ............................................................. 351/221
(58) Field of Search .................................... 351/205, 206, 351/209, 210, 211, 214, 221, 246; 600/477, 558

(56) References Cited

U.S. PATENT DOCUMENTS 4,883,061 * 11/1989 Zeimer ................................. 600/477

* cited by examiner

*Primary Examiner*—George Manuel
(74) *Attorney, Agent, or Firm*—Lowe Hauptman Gilman & Berner, LLP

(57) ABSTRACT

Disclosed is a three dimensional imaging scanning apparatus for retinal thickness and structure non-invasive analysis. The apparatus includes an optical path having a light source, common focusing optic and beam deflector for both incident and reflected beams going to and returning from the retina of an eye, and an imaging device. The apparatus further includes separate optical paths for imaging the fundus and iris of the eye. The speckles caused by retina non-uniformity can be removed by vibrating the common beam deflector during the image acquisition time. An eye model is obtained by spatially integrating images of the retina, the fundus and the iris.

27 Claims, 3 Drawing Sheets

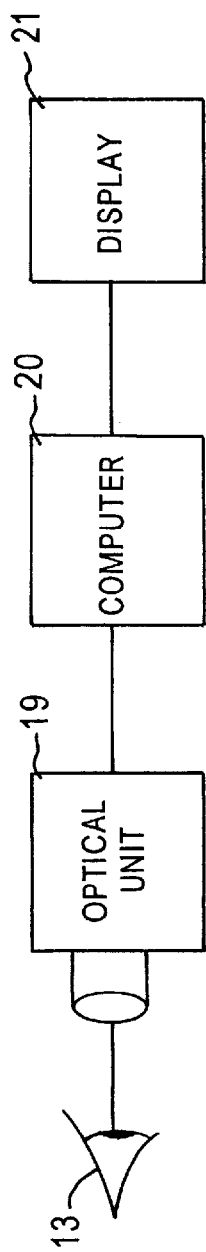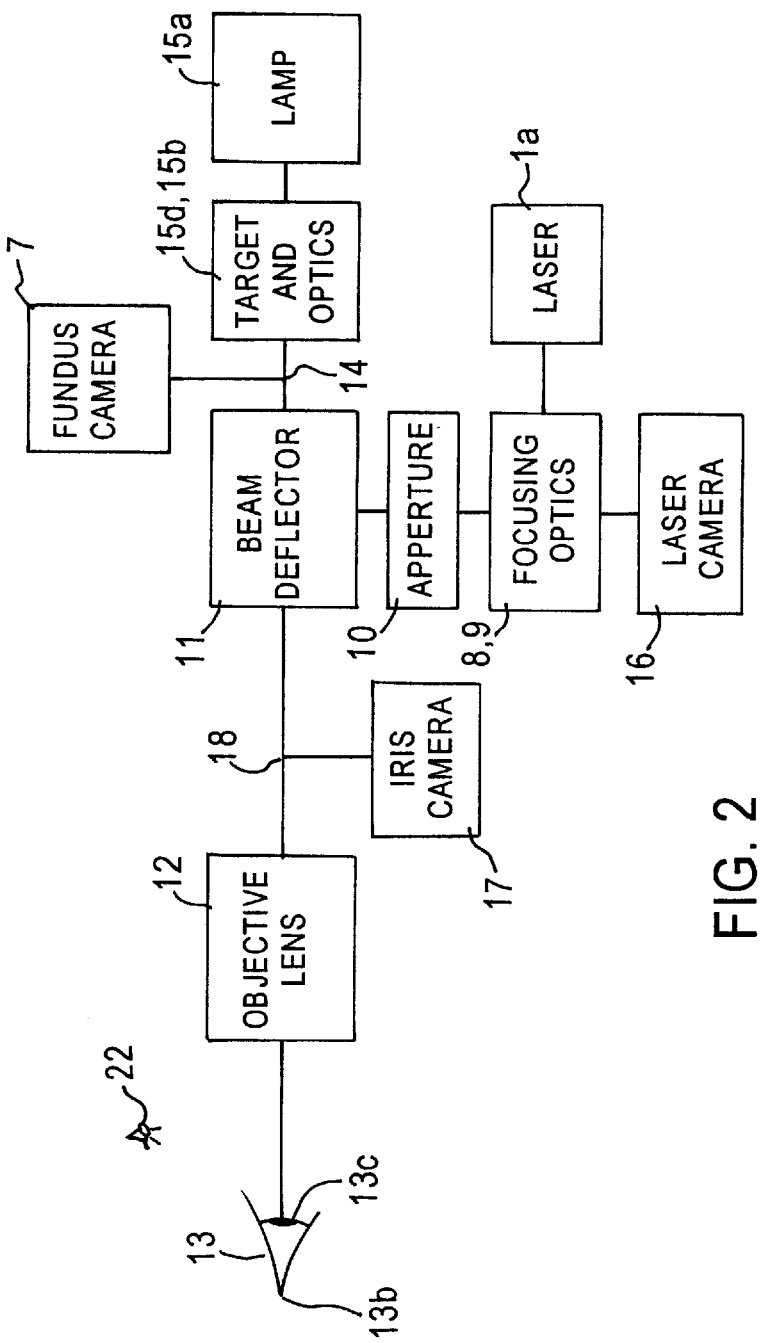

THREE DIMENSIONAL IMAGING APPARATUS AND A METHOD FOR USE THEREOF

FIELD OF THE INVENTION

The present invention generally relates to a three dimensional imaging apparatus and a method for use thereof. More specifically the present invention relates to a retinal tissue components size and thickness analyzer apparatus. The said invention furthermore relates to a non invasive measurement method for measuring retinal thickness imaging and for visualizing retinal cross sections by using said apparatus. The aparatus according to the said invention incorporates laser and conventional optics with computerizes signal analysis in order to measure pathological indications in the eye and in order to identify normal ocular physiology. This allows for improved diagnosis for various ophthalmic diseases such as diabetic retinopathy and glaucoma, and also for improved monitoring of therapeutic effects.

BACKGROUND OF THE INVENTION

The two main causes of blindness in the western world are diabetic retinopathy and glaucoma.

One of the most important pathologies of diabetic retinopathy is macular edema. Over a lifetime, about 30% of the people with diabetes will develop macular edema. Nonproliferative diabetic retinopathy with Clinically Significant Macular Edema (CSME) includes either (a) thickening of the retina at or within 500 microns of the center of the macular or (b) hard exudes at or within 500 microns of the center of the macular if associated with thickening of the adjacent retina (not residual hard exudates remaining after the disappearence of retinal thickening) or (c) a zone or zones of retinal thickening 1 disk area or larger, any part of which is within 1 disk diameter of the center of the macula. Patients with CSME should be considered for treatment.

The assessment of retinal thickening by slit lamp biomicroscopy and/or stereo fundus photography is often difficult, not accurate, and of questional reliability. Moreover, the current methods typically necessitate a time consuming involvement of a highly skilled observer. Currently there is no commercially available method, capable of detecting and mapping quantitatively retinal thickening. Thus accurate assessment of CSME in patients remains subjective even though the clinical criteria of CSME are quantitative. The present invention enables the necessary objective quantitative measurements to be performed.

Loss of vision from glaucoma is largely preventable through early diagnosis and therapy. While the level of Intra ocular Pressure (IOP) is strongly correlated with the risk of glaucoma optic nerve damage, a substantial proportion of patients with glaucoma (one sixth or more) have not had demonstratable or repeated elevations of IOP above 21 mm Hg. Conversely, many individuals with IOP repeatedly above 21 mm Hg do not have, and may never develop, optic nerve damage during their lifetime.

Screening procedures for identifying patients at significant risk for glaucomatous visual field loss are most effective when IOP measurements are combined with an assessment of the optic nerve and a review of other potential occular and systemic risk factors. This approach is already part of the "Comprehensive Adult Eye Examination", which may constitute the single most important screening/diagnostic setting to identify patients at risk and a subset of those at particularly "high risk" for glaucoma.

Visible structural alterations of the optic nerve or nerve fiber layer frequently occur before visual defects can be measured, even with the most sensitive current techniques. While measures of both structure and function are important to detect early glaucomatous damage, careful and repeated examination of the optic nerve and nerve fiber layer may provide the earliest signs of damage by demonstrating progressive damage before definitive visual field abnormalities appear. The present invention allows an objective method for nerve fiber layer damage assessment.

SUMMARY OF THE INVENTION

The present invention relates to a three dimentional imaging scanning apparatus for retinal thickness and structure non-invasive analysis. The present invention also relates to a method for the use of said apparatus.

The apparatus according to the present invention is comprised of at least one optical path having:

(A) A high brightness light source or a laser which provides a beam for illuminating a selected portion of the retinal tissue.

(B) A means for simultaneous focusing said beam going to the retina and returning from the retina wherein the said focusing means are common for both the beam going to and comming from the retina.

(C) An optical beam deflector which is common for both the beam going to and coming from the retina.

(D) An aperture for defining the angle between the beam going to the retina and returning from the retina.

(E) A detection means for detection of the returned beams and determination of the retinal thickness.

(F) A camera for imagining the pupil/iris is preferably added, which enables accurate longitudinal and perpendicular positioning of the beam from (A) on the pupil.

(G) A fundus camera for imagining the whole Fundus preferably added, which enables accurate longitudinal and perpendicular positioning of the beam from (A) on the retina.

The present invention further relates to a method for imaging the eye and its components using the apparatus according to the present invention, comprising;

(a) simultaneously using three optical paths for scanning the retina using a common optical beam deflector or deflectors to illuminate a predetermined zone of the retina and to acquire an image of said zone, while vibrating said beam deflector during said illumination/acquisition time, and said vibrations improve the image quality; imaging the whole Fundus; and imaging of the pupil/iris;

(b) subsequently spatially integrating one or more of said imagings into an eye model.

DETAILED DESCRIPTION OF THE INVENTION

The retinal thickness analyzer apparatus according to the present invention operates basically on the principle of slit lamp biomicroscopy. A narrow slit of light (laser light as a prefered embodiment) is projected onto the retina. The light scattered back from the retina is viewed by an electronic camera at an angle relative to the angle of the incident light. This provides a quantitative measurement of the retinal thickness cross-section topography for the specific retinal area selected and optical sectioning of the retina.

During one measurement the slit of light is scanned over a number of positions on the retina so that the resulting image represents a number of cross-sections of the retina covering a square area of for example 2×2 mm. It is possible for example that nine adjacent squares are scanned to provide coverage of about 6×6 mm (20°×20°) around the fovea, disk, or any other interesting zone. Likewise numerous contiguous or dispersed areas of the retina can be measured and the resulting three dimentional representations of the whole scanned area can be represented to enable a clinical and scientific evaluation. The retinal examination with the retinal thickness analyzer apparatus according to the present invention is performed in a manner similar to Fundus photography. After the eye is dilated and the patient is seated in the headrest of the apparatus, the apparatus is positioned along the optic axis of the eye at the correct working distance with reference to the iris display which shows a high magnification image of the iris of the examined eye. After alignment an image of the stationary slit on the retina is displayed, the focus adjustment knob is used to focus this image.

After focusing the scan is initiated. The display shows a set of slit images obtained at the positions scanned before. A thickness map, that can be displayed and/or stored for future reference, is generated by computer processing of the scanned slit images, within a short time. Different regions on the retina are scanned by translating the subjects fixation point. This is accomplished with the internal fixation target which is projected on the retina of the subjects eye. An external fixation light is also available for patients who have difficulty fixating on the internal target.

The present invention relates to a three dimentional imaging scanning apparatus for retinal thickness and structure non-invasive analysis. The present invention also relates to a method for the use of said apparatus.

The apparatus according to the present invention is comprised of at least one optical path having:

(A) A high brightness light source or a laser which provides a beam for illuminating a selected portion of the retinal tissue.

(B) A means for simultaneous focusing said beam going to the retina and returning from the retina wherein the said focusing means are common for both the beam going to and comming from the retina.

(C) An optical beam deflector which is common for both the beam going to and comming from the retina.

(D) An aperture for defining the angle between the beam going to the retina and returning from the retina.

(E) A detection means for detection of the returned beams and determination of the retinal thickness.

In the preferred embodyment of the present invention optical paths and cameras are included for imaging both the whole Fundus and the pupil/iris.

These five apparatus elements allow the retinal thickness and structure non-invasive measurement to be performed. For purposes of accomplishing said measurement for a specific region of the retina, whole fundus imaging and imaging of the pupil/iris is used. The fundus imaging is specifically employed to provide psysiological spatial orientation when selecting and also when subsequently comparing specific regions of the retina. The pupil/iris imaging is specifically employed to allow selection of a point like region of the pupil plane, having acceptable or advantageous optical properties. This point like region serves as the window through which the actual retinal measurement is accomplished.

The present invention will be further described in detail by FIGS. 1–4. These figures are solely intended to illustrate the prefered embodiment of the invention and are not intended to limit the scope of the invention in any manner.

FIG. 1 illustrates a block diagram of the device according to the present invention.

FIG. 2 represents a block diagram of the optical unit of the device.

DETAILED DESCRIPTION OF THE FIGURES

Figure 3:
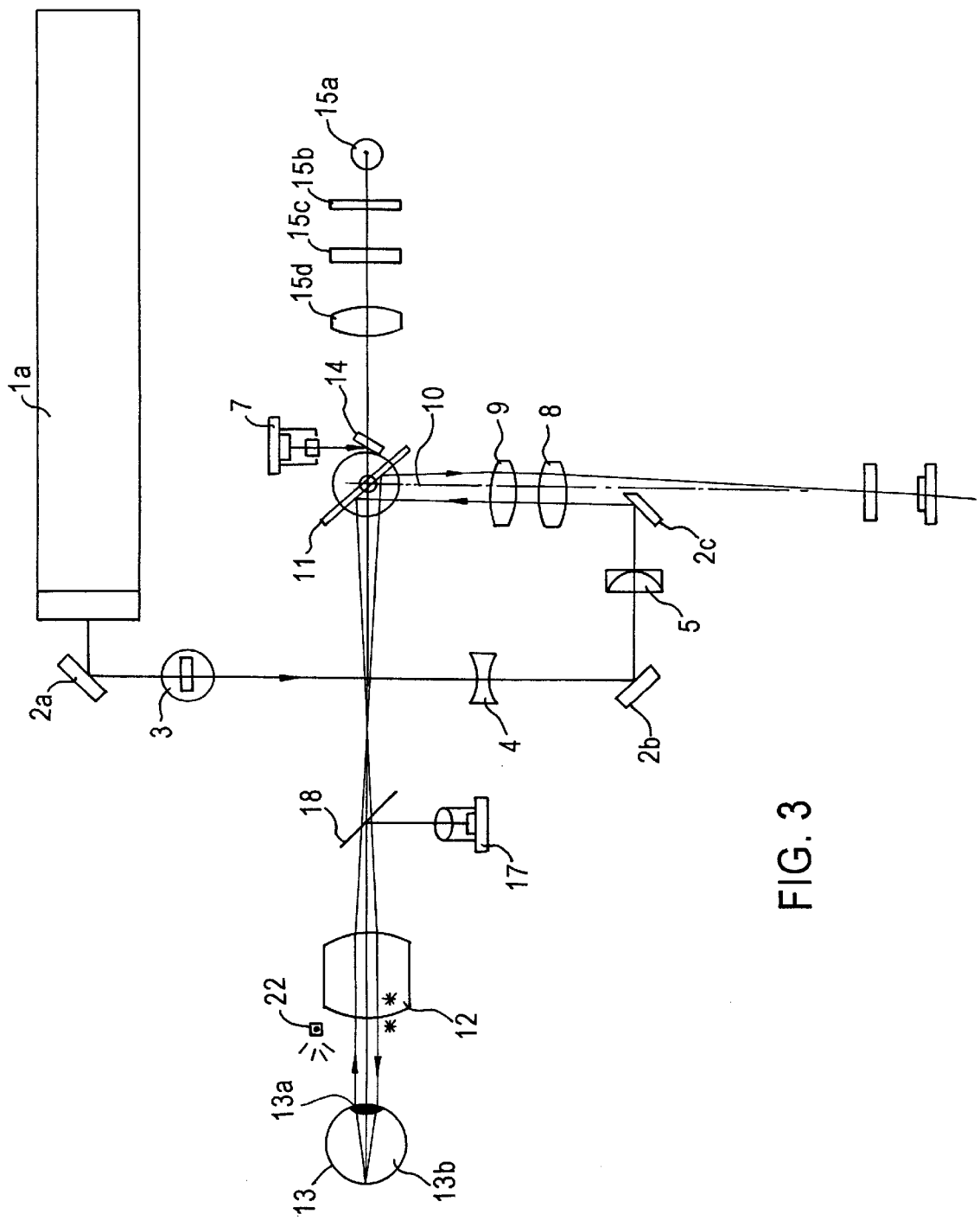
FIG. 3 is a schematic illustration of the major electro-optical components of the present invention.

FIG. 1 illustrates a block diagram of the device according to the present invention. An optical unit (19) illuminates the eye (13) including the retinal tissue contained therein. The light returns from the eye to the optical unit where said light is measured by optical sensors. The electronic signal from the optical sensors is transmitted to a computer processor (20). The computer processor displays representations and composite imagery on a display monitor (21).

FIG. 2 represents a block diagram of the optical unit of the device. In the optical unit [(19) in FIG. 1] of the apparatus according to the present invention, light originating from a light source (15a) (halogen lamp) passes through a condenser lens (15d) (collimator lens), passes through a target pattern (15b) where the target pattern is imposed filter-wise onto the light. The light thus filtered passes through or under a common beam deflector (11). The light then proceeds through a objective lens (12) and onto the eye (13) and its inner tissues. Some portion of this incident light is reflected back through the same objective lens (12), through or under the beam deflector (11) and to a fundus mirror (14) where the returning reflective light is sensed by a fundus camera (7).

A second optical path in the optical unit begins with light originating from an eye illuminating light source (22) (for example an iris illuminating LED) which directly illuminates the eye (13). Light reflected back from the iris (13c) passes through the objective lens (12) and is reflected by a beam splitter (18) (e.g. dichroic mirror for near intra-red) where the returning reflected light is sensed by an iris camera (17) (e.g. sensative to near infra-red).

A third optical path in the optical unit begins with a light beam originating Prom a laser (1a) and passing through shaping and focussing optics (8) (9). The light beam so attenuated and modified is then reflected through an aperture (10) and through the common beam deflector (11) where organized time dependent angular variations are imposed onto the light beam. The beam then passes through the common objective lens (12) and onto the eye (13) and its retinal tissues (13b). Returning scattered light from the retinal tissues passes back through the objective lens, beam deflector, lenses (9) (6), aperture (10), and is detected by the laser camera (16) (CCD).

FIG. 3 represents a profile schematic illustration of the major electro-optical components of the present invention apparatus. A coherent monochromatic laser beam (1) (or a very bright light source) in green (or yellow or orange) e.g. 543 nm originated from a Here laser (1a) (also may be other types of lasers or a bright diode or a high brightness lamp) is reflected by a mirror (2a) and passing through an attenuator (3) (at least one attenuator). The attenuator may be mounted on a solenoid (so that changes in the solenoid's position allow for changes in the intensity exiting from the attenuator). Thus the light exiting from the attenuator is in compliance with the FDA (Food and Drug Administration—USA) standards and requirements for limiting the itensity of the light exposure to the retina. The attenuated light also allows for compensation in eyes of different scattering coeficients.

The laser beam traverses a negative lens (4) (may also be a positive lens) which is the first part of the beam expander and which widens the beam. Thereafter the widened beam is reflected by a mirror (2b), passes through a cylindrical lens (5) changing the beam profile so that the subsequent profile of the beam at the retina is slit shaped and not dot shaped. The lens position and focal length is such that the beam cross section is small enough to traverse the eye's pupil. The laser beam is then reflected by a mirror (2c) and traverses through one side of a positive lens (8) which is the second lens of the laser beam expander, and this positive lens (8) is the complimentary corective step to the negative lens (4). This composite beam expander insures appropriate width on the fundus. It should also be noted that by "one side" of lens (8) we mean to a position which is off axis of the lens. In another embodiment of the present invention this off-of-center optic geometry may not be used.

From this lens (8) goes out a parallel beam to focus lens (9). This lens, the focus lens, is focusing the beam to a small dot in a focal distance between lenses (9) and (12) and subsequently the beam passes through the focal plane of objective lens (12). Movement along the optic axis of focus lens (9) enables compensation for refractive variations in the eye to be examined. The laser beam then is reflected by the common beam deflector (11), or by any other optical scanner known in the art such as holographic or acoustoptic. This beam deflector is a small thin mirror with a small scanning angle and a fast response time. The common beam deflector (11) is near the location of the image of the pupil (13a) of the patient. Because the laser beam is falling on the mirror at a point which is not perturbed by minor changes of the mirror's angle, this beam will fall on a predetermined point near the pupil that likewise will not move during the scanning. Lenses (4) (5) (8) (9) and (12) constitute a beam shaping unit for insurring appropriate width and height of the beam on the fundus.

It is possible to insert a holographic or electro-optic element near the location of the image of the pupil (13a) of the patient. This element will split the laser beam into multiple beams, so that on the retina more than one laser line will be simultaneously projected.

The laser beam from the common beam deflector (11) goes to the objective lens (12) from which it goes out in parallel beam (when working with emmetropic eye). This parallel beam will rotate to the sides during the rotation of the common beam deflector (11). This rotation of the beam will cause the laser line on the retina to move. The beam deflector mirror will move to enable the laser slit profile to move 2 mm on the retina (13b).

Part of the scattered light from the retinal layers returns through the iris (13c) and the objective lens (12) to the common beam deflector (11). This light passes through an aperture (10) located near the plane of the pupil image so as to define the area on the pupil of collected scattered light. The distance between the laser beam and the aperture (10) at the aperture area defines the distance at the area of the pupil between the incident beam and the measured scattered beams ultimately going to the CCD camera (16).

The reflected beam is passing through a focus lens (9). In the place where there is a focus adjustment for the laser beam, the scattered beam from the eye makes a parallel beam to the incident beam between lens (8) and (9). The focus adjustment is necessary in order to compensate refractive error in the examined eye. The beam returning through lens (8) becomes focused into a sharp image in a focal plane.

There is a CCD camera (16) located in said focal plane. This CCD camera receives the scattered light returning from the retinal tissue. At the entrance to the CCD camera there is a filter (6) which transfers the scattered laser light but blocks both direct and scattered lamp light.

The lenses (a) and (9), the aperature (10), and the mirror (2c) are near the common beam deflector (11). In this way it is guaranteed that there is no overlapping between the incident beam to the eye and the scattered laser beams returning from the eye and comming to the CCD camera.

The lenses (8) and (9), the common beam deflector (11), and the objective lens (12) are common optical elements. The incident laser beam passes through these elements or is reflected by them prior to interaction with the eye components, and also subsequent to said interactions. The scattered laser light returns through these same elements before hitting the CCD camera. Because these optical elements are common to both the incident and the scattered light, any small movement of one of these optical elements will not cause the apparatus to diverge from correct adjustment this is because the error introduced into the incident beam by one of the elements is by definition exactly compensated for by the same element when the scattered return beams pass through or are reflected by said element.

Because the focussing lenses are common optical elements, only one focus element adjustment is necessary since this single adjustment corrects both the incident focus and the scattered return focus. Were this rat the case, it would be necessary to adjust the incident optical element and the scattered return optical element.

Because the beam deflector is one of the above-mentioned common optical elements (both for the incident and reflected laser beams), the retinal slit image will not move on the CCD camera during scanning. This enables using a camera of small dimensions in the scan ass, even when a very wide area is scanned on the retina.

We can also locate the camera so that the laser's narrow and long slit image is parallel to the horizontal pixels of the camera, effectively lowering the needed bandwidth and number of pixels of the camera in this dimension without losing retinal thickness details.

We can move the aperture (10) and by this movement we are changing the angle between two beams—the incident beams to the retina and the scattered beams from the retina. This also changes the distance between the laser beam incident an the cornea, and detected scattered beam from the retina through it thus enabling a change in the zone used in the pupil. Because the incident and scattered beams are close one to the other, and even given the small aperture opening of the dilated pupil, the best zone in the cornea and the dilated pupil Can be selected for use. Thus there exists the possibility to shift the location on the cornea through which the incident and scattered beams will traverse, thus allowing the avoidance of optical or physical defects in the cornea.

The apparatus according to the present invention has also a halogen lamp (15a). The light from the halogen lamp (15a) goes through a colimator lens (15d) and is then projected to the objective lens (12). Near the colimator lens (15d) there is a target pattern (15b) inscribed with the image of numbers one through nine. In the light path of the halogen lamp there is a filter (15c) (green, yellow, orange) for selection of the most appropriate light for Fundus photography. This halogen lamp light passes near the common beam deflector (11) in the incident direction and is collected and directed to a Fundus camera (7) by a fundus mirror (14). Near the beam deflector an aperture is located in the way of the scattered beam so that there is no overlap between the incident and the scattered beams. This eliminates cross talk between the beams in order to obtain a good contrast in the fundus image.

Near the objective lens (12) there is a light source (22) (iris illuminating LED) which illuminates the eye, and a dichroic mirror (18) (beam splitter) (which reflects a light wavelength that is not used by the laser camera nor by the Fundus camera (e.g. Near Infra-red light), and this wavelength is used in the iris imaging). This mirror reflects light from the cornea to a camera (17) (iris camera) for imaging of the pupil and the iris.

The apparatus according to the present invention has three electronic cameras: a CCD camera (16) for imaging the retinal thickness, a fundus camera (7) for imaging the whole Fundus, and a third camera (17) for imaging the pupil/iris.

The video from the three cameras is trasfered to a computer by a frame grabber card, processed, and displayed on a screen or screens. Also on the same screen or another screen is at least one text area, the content of which is determined through an operator interface.

Prior to initiating the retinal thickness measurements, the operator sees the tripartite composite image an the screen, except the the laser beam scan area is outlined. This allows the operator to select (a) the desired area of the fundus for the subsequent thickness measurement as defined by the outline, (b) the optimal settings for acquiring the area in the cornea through which said measurement will be performed as is evident from the response of the sample laser slit pattern quality, (c) optimal focus of the slit image.

Because the retinal thickness measurement image is slit shaped for each measurement taken and because for each such measurement taken during a given scan series said slit pattern is central to the CCD derived image, computer processing is required to integrate the beam deflector orientation with the corresponding image so that the image series can be properly organized with respect to corresponding locations on the retina. Said organization for a single scan series is a collection of parallel slit images. For example if we scan a 2 mm section of the retina then the beam deflector iteratively measures and jumps 200 μm until it completes the 2 mm section and this results in a parallel series of 10 slit shaped thickness profiles. The image of the laser slit scattered from the retina is composed of (a) scattering signal from the two layers that are at the edges of the retina (Pigment Epithelium—Choroid layer and Inner limiting membrane), and (b) a signal from the internal volume between those layers. Sometimes (c) a signal is seen from other layers and material near the retina, for example the membranes.

The image processing algorithm calculates the distance between the two peak signals that represent the two sides of the retina. This calculation is performed on the slit images every given 200 μm distance along the length of the laser slit.

After image processing, various representation formats can be selected to allow for the best use of the mapping of thickness data. For example: (a) iso-thickness coountour lines can be drawn, (b) a false coloration scale can be imposed in a thickness relevant fashion, (c) the data can be graphed onto various coordinate systems so as to allow best visualization of potential causal correlations, (d) comparative transformations with previous imagery for the same area for the same patient or according to demographic, genetic, physiological, or other factors can be represented, (e) numeric values for patient treatment evaluation and for comparison with previous or future results.

The aparatus according to the present invention can be adjusted to scan different locations of the retinal tissue. This is accomplished by directing the patient to fixate on one of the numericly labled locations on a projected target image (15b). Alternately the patient can be directed to fixate with the other eye on a small light source which the operator can move, and this causes the eye to be measured to fixate in a parallel-like fashion.

The area of the retina to be measured appears on the apparatus's computer monitor as a square outline superimposed on the imagery from the Fundus camera. The basic square outline in the preferred embodiment of the present invention coresponds to a region of 2 mm×2 mm on the retinal tissue. Subsequently to the scanning measurement, the thickness profile data is saved in association with the Fundus imagery so that in subsequent representations of the measurements, multiple measured areas can be shown simultaneously. The operator or the computer can select at least one "landmark" on the fundus to allow fundus images to be aligned. A "landmark" can be an easily identifyable blood vessel bifurcation or a morphologic anomaly. This use of landmarking helps guarantee that both the tiling of contiguous squares and their relation to other dispersed square regions will be represented with the proper spatial relationship.

When either a light source with a long coherence length is used or when the area being measured scatters light in a non-uniform manner, the subsequent measurement of the cross sections of the slit shaped beam as scattered from the retinal tissue is noisy. The resultant picture is characterized by rapid changes in signal intensity, originating from macroscopic structure in the area. The effect of this noise in the region of any given cross section is to cause the otherwise clear bi-modal intensity distribution corresponding to the thickness of the retinal tissue to be a multi-modal intensity distribution, which leaves the thickness measurement interpertation of the data in an ambiguous state.

In a prefered embodiment of the present invention this noise problem is eliminated through a signal averaging procedure called "speckle removal". The speckle removal technique is a type of neighborhood averaging wherein the scanned area is moved slightly during the actual measurement. This may slightly reduces the lateral resolution with regard to positioning on the retina but greatly reduces the thickness measurement ambiguity problem. This technique can be used because the CCD camera receives scattered return light from the retina through the same beam deflector as the emitted light to the retina, thus guaranteeing that the image on the CCD stays sharp, since the image of the laser line that moves on the retina does not move and smear the image on the CCD while the small amplitude scan is performed.

For example, we take an image within 0.02 sec of the scattered laser line on the retina. The laser line width on the retina is 20 μ. Speckles and retinal non-uniformity size is 30 μ. During this time (0.02 sec) we move the laser beam on the retina 75 μ across the beam length. The scattered light is composed of the spatial average signal for the whole zone over which the laser beam moved during the imaging time. In this image too, speckles and retinal non-uniformities are averaged and therefore their noise is reduced. The image on the imaging device is not smeared due to the movement of the laser beam since it uses the same beam deflector mirror and optical path.

Super-imposed movements (vibrations) of predetermined amplitude and shape, and are super-imposed onto the normal motion of the optical beam deflector for use in speckles removal subsequent to detection. Said super-imposed movements of the beam deflector are such that the beam exposes every point on the target equally (with the same amount of light) during acquisition time.

The method for speckles removal of the present invention reduces optical noise caused by retina (target) non-uniformity, said super-imposed movements (A) move the illuminating zone over an area larger than that zone, (B) concurrently move the imaging zone so that the image of the illuminated zone does not move on the imaging device (even though it was scanned over a zone larger than the instantaneously illuminated and/or imaged zone), and (C) does this process in a time shorter than the image acquisition time.

The focus of the picture is very important. The operator adjusts the focus lens (9) to get as sharply focused a picture as is possible. The operator subjectively determines this from the definition of a slit image on the retinal tissue that the operator sees on the apparatus's computer monitor. Another option to achieve focus adjustment is to adjust the focus lens until the slit profile corresponding to the center of the area to be measured appeares on the monitor at a preset point at which the slit appears when the system was calibrated.

The camera for imaging the pupil/iris produces an image of the eye being checked. The operator can observe the pupil and adjust the vertical and horisontal position for the apparatus in order to select a prefered section of the cornea through which the retinal measurement is to be executed. This image is focused by the operator by adjusting the distance between the apparatus and the patient's eye. The F number of this camera's lens is small and therefore the depth of field of the focus is small. Once the image is sharp, the distance from the system to the patient's iris is always the same as when adjusted while calibrating the system.

Figure 4:
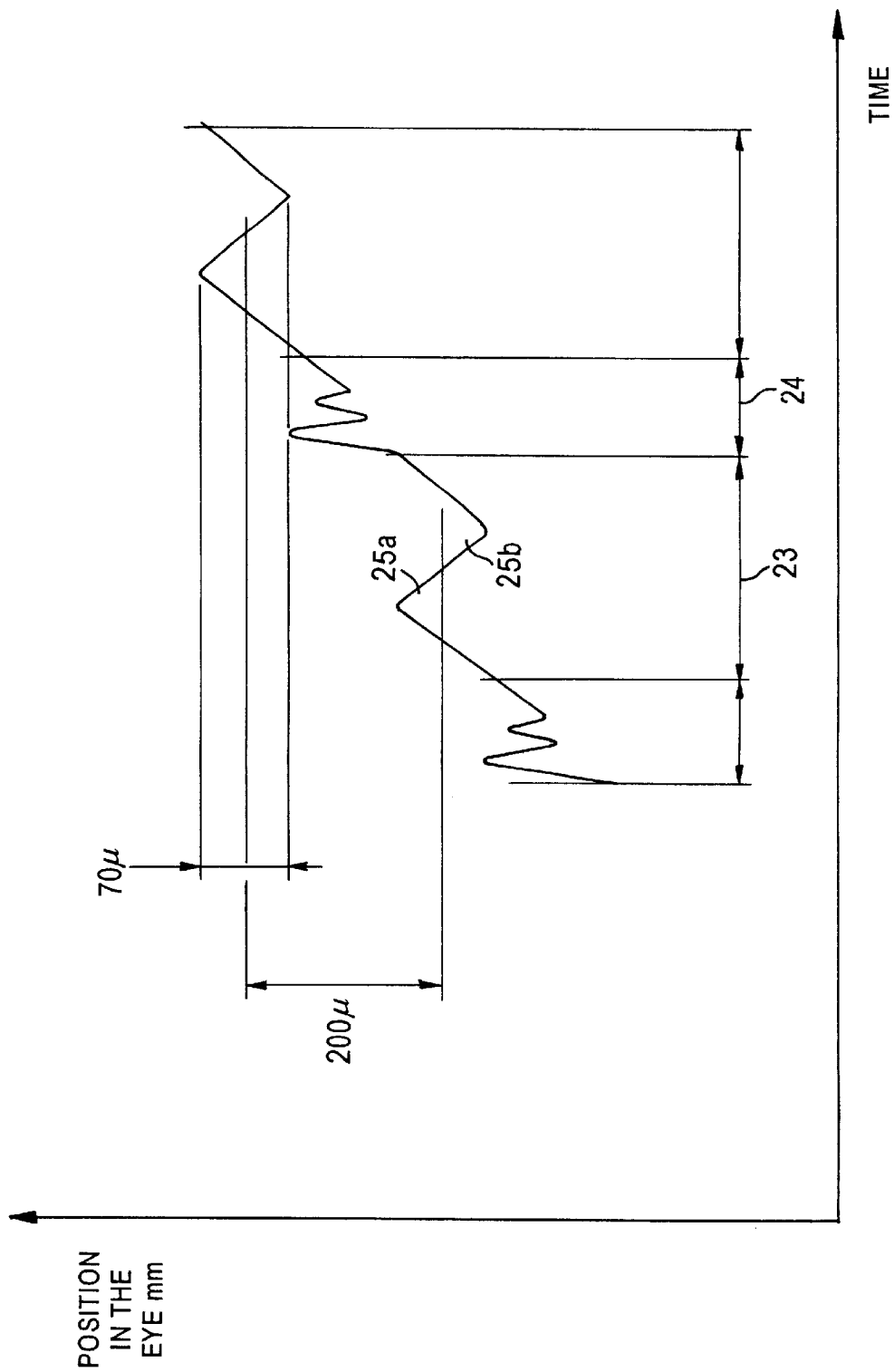
FIG. 4 represents a schematic graph of beam position in the eye versus time.

FIG. 4 represents a schematic graph of beam position in the eye versus time. The time axis is divided into windows of image aqusition (23) and non-imaging windows (24). The beam position in the eye during the image acqusition window remains fixed with oscilation imposed, such that every point on the targer is equally exposed. During the non-imagining window the position of the beam is moved to its next location.

Assume that every frame (every 40 msec) the image from the CCD is stored. This image is called a slit image. During the CCD Vertical Fly Back time, the beam deflector jumps to the next location which is shifted 200 $\mu$ on the retina. This process is repeated 10 times so that the slit images cover an area 2 mm wide.

In order to operate the Speckle Remover, the beam deflector is vibrated while an image is being acquired. The vibration amplitude on the retina is larger than the speckle or the non-uniformity size, for example 70 $\mu$. The vibration can be composed of an integer number of back and forth movements during this time. The image on the CCD is not blured due to this movement since it images the retina thru the same beam deflector that moves the laser beam on the retina.

Still the optic signal collected is from the whole area that was illuminated by the laser during the operation of the speckle remover. Since area (25a) is equal to area (25b), the camera receives a homogeneous blur of the speckle remover zone.

The present invention also relates to a method for imaging the eye and its components using the apparatus as defined, comprising;

(a) simultaneously using three optical paths for scanning the retina using a common optical beam deflector or deflectors to illuminate a predetermined zone of the retina and to acquire an image of said zone, while vibrating said beam deflector during said illumination/acquisition time, and said vibrations improve the image quality; imaging the whole Fundus; and imaging of the pupil/iris;

(b) subsequently spatially integrating one or more of said imagines into an eye model.

In the method according to the present invention the eye model may be represented in a format for retinal thickness mapping data (a) visualized as iso-thickness countour lines, (b) with a false coloration scale imposed in a thickness relevant fashion, (c) graphed onto various coordinate systems, for visualization of potential causal correlations, (d) for comparative transformations with previous imagery for the same area of the eye for the same patient, or according to demographic, genetic, physiological, or other factors, or (e) for quantitative evaluation, patient treatment, and comparison with previous or future results.

What is claimed is:

1. A three dimensional imaging scanning apparatus for retinal thickness and structure non-invasive analysis, said apparatus comprising at least one optical path having a light source providing an incident beam for illuminating a selected zone of a retina of an eye;

a focusing optic for simultaneously focusing said incident beam going to the retina and a reflected beam returning from the retina, wherein the focusing optic is common for both the incident beam and the reflected beam;

an optical beam deflector common for both the incident beam and the reflected beam;

an aperture for defining an angle between the incident beam and the reflected beam; and a detector for detecting the reflected beam and for determining a thickness of the retina.

2. The apparatus according to claim 1, further comprising a second optical path having an iris light source illuminating an iris of the eye, and an iris camera for sensing a second reflected beam returning from the iris.

3. The apparatus according to claim 1, further comprising a third optical path having a fundus light source illuminating a fundus of the eye, and a fundus camera for sensing a third reflected beam returning from the iris.

4. The apparatus according to claim 3, wherein the fundus light source is a halogen lamp.

5. The apparatus according to claim 1, wherein the light source is selected from the group consisting of a coherent monochromatic laser, a bright diode, and an arc lamp.

6. The apparatus according to claim 5, wherein the light source provides or can be filtered to provide substantially green, yellow, or orange light.

7. The apparatus according to claim 1, further having a beam shaping unit for insuring appropriate width and height of the beam on the retina.

8. The apparatus according to claim 1, further having at least one attenuator in the optical path for limiting the intensity of light exposure to the retina.

9. The apparatus according to claim 1, wherein the detector is a CCD camera.

10. The apparatus according to claim 1, wherein the incident beam and the reflected beam are received and transmitted by the common optical beam reflector in substantially same optical path.

11. A method of speckles removal for use in a retinal analysis using a common optical beam deflector for both illuminating an incident beam on a selected zone of a retina and transmitting a reflected beam returning from the retina to an imaging device for acquiring an image of the retina, said method comprising the steps of super-imposing super-imposed movements onto motion of the optical beam deflector to move the illuminated zone on the retina over an area larger than that zone, thereby concurrently moving the imaging zone so that the image of the illuminated zone does not move on the imaging device, and finishing the super-imposed movements within a time shorter than an image acquisition time.

12. A method for imaging eye components, comprising the steps of (a) simultaneously using three optical paths for
   (i) scanning and imaging an retina of the eye using at least a common optical beam deflector to illuminate a predetermined zone of the retina and to acquire an image of said zone, while vibrating said optical beam deflector during an illumination/acquisition time to improve image quality;
   (ii) imaging a Fundus of the eye; and
   (iii) imaging a pupil/iris of the eye;

(b) subsequently spatially integrating one or more of said imagings into an eye model.

13. A method according to claim 12 wherein the eye model is represented in a format for retinal thickness mapping data visualized as iso-thickness countour lines.

14. A method according to claim 12 wherein the eye model is represented in a format for retinal thickness mapping data with a false coloration scale imposed in a thickness relevant fashion.

15. A method according to claim 12 wherein the eye model is represented in a format for retinal thickness mapping data graphed onto various coordinate systems, for visualization of potential causal correlations.

16. A method according to claim 12 wherein the eye model is represented in a format for comparative transformations with previous imagery for the same area of the eye for the same patient, or according to demographic, genetic, physiological, or other factors.

17. A method according to claim 12 wherein the eye model is represented in a format for quantitative evaluation, patient treatment, and comparison with previous or future results.

18. A three dimensional imaging scanning apparatus for retinal thickness and structure non-invasive analysis, said apparatus comprising at least one optical path having a high brightness light source or a laser providing a incident beam for illuminating a selected zone of a retina;

a focusing optic for simultaneously focusing said incident beam going to the retina and a reflected beam returning from the retina, wherein the said focusing optic is common for both the incident beam and the reflected beam;

an optical beam deflector common for both the incident beam and the reflected beam, wherein super-imposed movements of a predetermined amplitude are super-imposed onto motion of the optical beam deflector for reducing optical noise caused by non-uniformity of the retina;

an aperture for defining an angle between the incident beam and the reflected beam; and a detector for detecting the reflected beam and for determining a thickness of the retina.

19. The apparatus according to claim 18, further comprising a second optical path having an iris light source illuminating an iris of the eye, and an iris camera for sensing a second reflected beam returning from the iris.

20. The apparatus according to claim 18, further comprising a third optical path having a fundus light source illuminating a fundus of the eye, and a fundus camera for sensing a third reflected beam returning from the iris.

21. The apparatus according to claim 20, wherein the fundus light source is a halogen lamp.

22. The apparatus according to claim 18, wherein the light source is selected from the group consisting of a coherent monochromatic laser, a bright diode, and an arc lamp.

23. The apparatus according to claim 22, wherein the light source provides or can be filtered to provide substantially green, yellow, or orange light.

24. The apparatus according to claim 18, further having a beam shaping unit for insuring appropriate width and height of the beam on the retina.

25. The apparatus according to claim 18, further having at least one attenuator in the optical path for limiting the intensity of light exposure to the retina.

26. The apparatus according to claim 18, wherein the detector is a CCD camera.

27. The apparatus according to claim 18, wherein the super-imposed movements of the optical beam deflector cause the incident beam to illuminate every point of the selected zone equally during an acquisition time.

* * * * *